(12) United States Patent
Iwazaki et al.

(10) Patent No.: US 6,711,932 B2
(45) Date of Patent: Mar. 30, 2004

(54) ABNORMALITY DIAGNOSIS SYSTEM AND METHOD FOR OXYGEN SENSOR

(75) Inventors: Yasushi Iwazaki, Susono (JP); Kazuhiro Yamada, Toyota (JP); Takashi Ogawa, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 10/176,527

(22) Filed: Jun. 24, 2002

(65) Prior Publication Data
US 2003/0005746 A1 Jan. 9, 2003

(30) Foreign Application Priority Data
Jul. 4, 2001 (JP) ........................................ 2001-203592

(51) Int. Cl.[7] .............................................. G01N 27/00
(52) U.S. Cl. ..................... 73/1.06; 73/23.31; 73/23.32; 73/31.05
(58) Field of Search ................................. 73/1.06, 31.05, 73/23.32, 23.31; 422/94; 123/688, 690

(56) References Cited

U.S. PATENT DOCUMENTS 5,819,195 A  10/1998  Iwata ........................ 701/103

FOREIGN PATENT DOCUMENTS

| JP | A 5-125978 | 5/1993 |
| JP | A 5-256175 | 10/1993 |
| JP | A 8-21282  | 1/1996 |
| JP | A 10-10080 | 1/1998 |

*Primary Examiner*—Daniel S. Larkin
(74) *Attorney, Agent, or Firm*—Oliff & Berridge, PLC

(57) ABSTRACT

An oxygen sensor includes a detector to be positioned between the ambient air and the exhaust gas, which generates a voltage corresponding to a difference in oxygen partial pressure therebetween. A controller performs monitoring of the output voltage from the oxygen sensor and determines an occurrence of fracture in the detector when detecting the generation of a lean signal, which is a signal indicating the above-described difference in the oxygen partial pressure is small, being frequently more than a certain value, and carries out an abnormality diagnosis to the oxygen sensor.

20 Claims, 10 Drawing Sheets

10-INTERNAL COMBUSTION ENGINE
11-INTAKE AIR PASSAGE
12-COMBUSTION CHAMBER
13-EXHAUST PASSAGE
14-AIR CLEANER
15-THROTTLE VALVE
16-AIRFLOW METER
17-INJECTOR
18-CATALYST
19-FRONT OXYGEN SENSOR
20-REAR OXYGEN SENSOR
21-ACCELERATOR SENSOR

FRACTURE OF DETECTING PORTION

EXHAUST GAS FLOWING TO INSIDE OF DETECTING PORTION

IMMEDIATELY AFTER STOP OF FUEL CUT (F/C)

10-INTERNAL COMBUSTION ENGINE
11-INTAKE AIR PASSAGE
12-COMBUSTION CHAMBER
13-EXHAUST PASSAGE
14-AIR CLEANER
15-THROTTLE VALVE
16-AIRFLOW METER
17-INJECTOR
18-CATALYST
19-FRONT OXYGEN SENSOR
20-REAR OXYGEN SENSOR
21-ACCELERATOR SENSOR

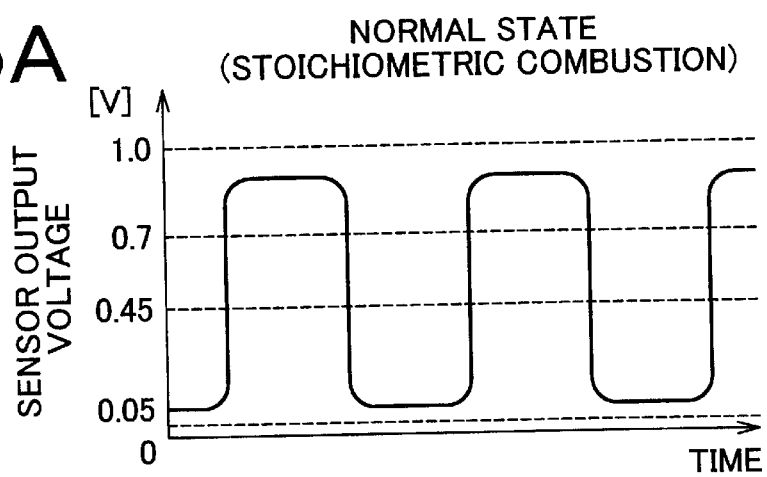
FIG. 5A  NORMAL STATE (STOICHIOMETRIC COMBUSTION)
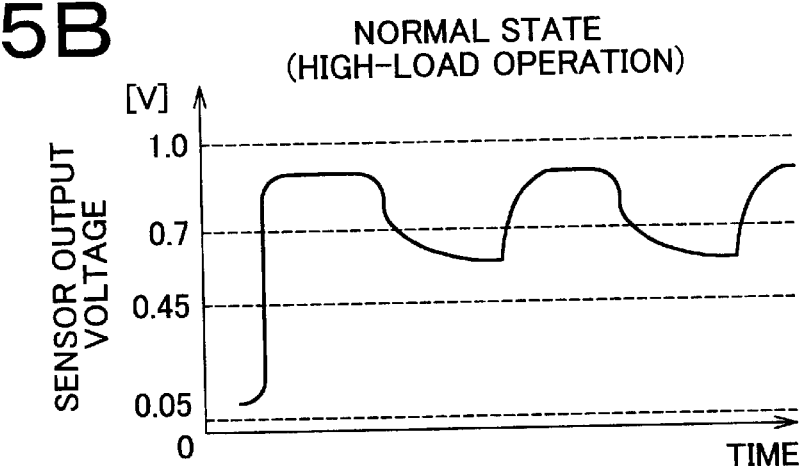
FIG. 5B  NORMAL STATE (HIGH-LOAD OPERATION)
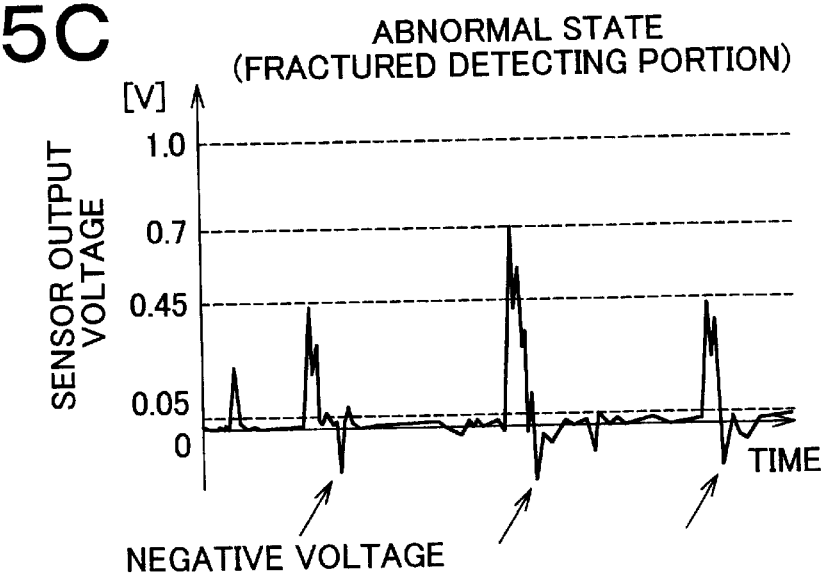
FIG. 5C  ABNORMAL STATE (FRACTURED DETECTING PORTION)

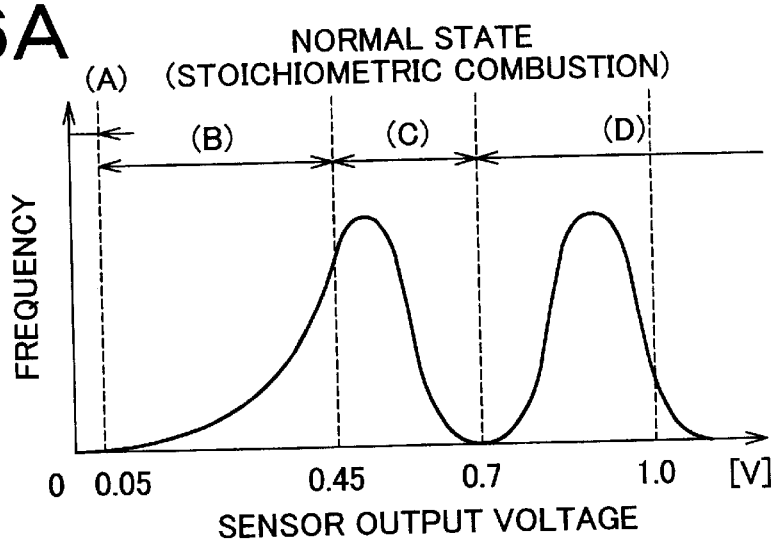
FIG. 6A NORMAL STATE (STOICHIOMETRIC COMBUSTION)
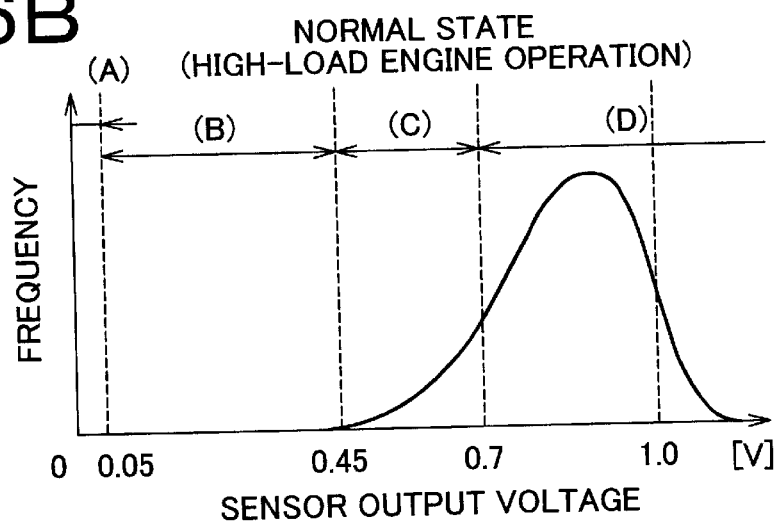
FIG. 6B NORMAL STATE (HIGH-LOAD ENGINE OPERATION)
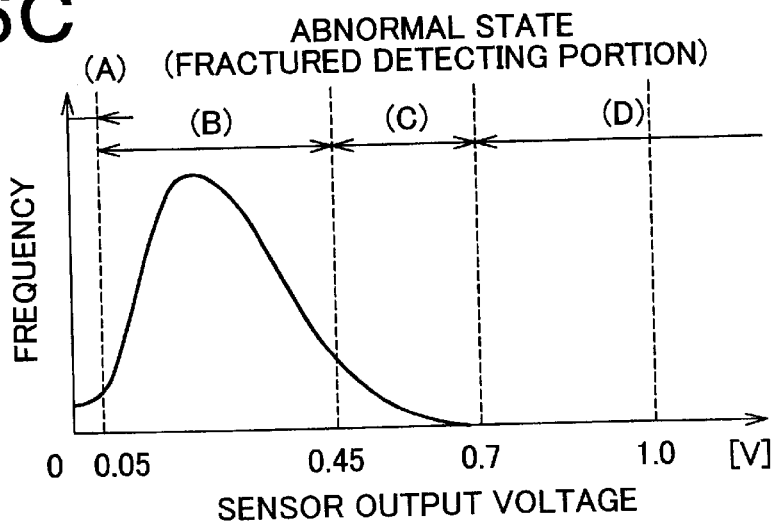
FIG. 6C ABNORMAL STATE (FRACTURED DETECTING PORTION)

ABNORMALITY DIAGNOSIS SYSTEM AND METHOD FOR OXYGEN SENSOR

INCORPORATION BY REFERENCE

This disclosure of Japanese Patent Application No. 2001-203592 filed on Jul. 4, 2001 including the specification, drawing and abstract is incorporated herein by reference in its entirety.

BACKGROUND OF THE INVENTION

1. Field of Invention

The invention relates to an abnormality diagnosis system and method for an oxygen sensor. More particularly, the invention relates to an abnormality diagnosis system and method which performs a diagnosis on an abnormality of the oxygen sensor caused by its fractured detector.

2. Description of Related Art

In an internal combustion engine which includes an exhaust purification system utilizing a catalyst, it is essential to accurately control an air-fuel ratio of an air-fuel mixture which is combusted in the internal combustion engine such that the catalyst effectively purifies exhaust gas emission. The air-fuel ratio is defined as a weight ratio of the air to the fuel contained in the air-fuel mixture for combustion. In the internal combustion engine requiring the aforementioned highly accurate control of the air-fuel ratio, an oxygen sensor for detecting a partial pressures of oxygen (hereinafter referred to as oxygen partial pressure) in exhaust gas is provided in an exhaust system of the engine. The air-fuel ratio obtained on the basis of the detected partial pressures of oxygen is used for executing feedback control of the air-fuel ratio.

By way of an example, a tubular oxygen sensor utilizing a solid electrolyte will be described. FIG. 1 shows a conceptual structure of the tubular oxygen sensor (hereinafter referred to as an "oxygen sensor"). As shown in FIG. 1, the oxygen sensor includes a tubular detector that extends into an exhaust passage. An inside of the detector is exposed to the atmosphere whereas an outside thereof is exposed to the exhaust gas that flows into the detector through a sensor cover that surrounds the detector. The detector is made of a solid electrolyte and the inside and outside of the detector are covered with electrodes as shown in FIG. 1. The solid electrolyte is a solid substance that allows movement of an ionized oxygen. For example, zirconia is typically used as the solid electrolyte for the oxygen sensor.

As shown in FIG. 1, a difference of the oxygen partial pressure is caused between the atmosphere (inside of the detector) and the exhaust gas (outside of the detector) which has been isolated via the detector. In this state, the oxygen in a high oxygen partial pressure side (normally the atmosphere side) is ionized and the resultant oxygen ion moves to a low oxygen partial pressure side (normally the exhaust gas side) so as to reduce the difference of the oxygen partial pressure. The oxygen molecule receives four electrons into an ionized state, and releases four electrons into an unionized state. In the course of the movement of the oxygen molecules, electrons move between the electrodes formed on the inside and outside of the detector, generating an electromotive force. Accordingly, the oxygen sensor generates a voltage corresponding to the difference in the oxygen partial pressure between the atmosphere and the exhaust gas.

The oxygen partial pressure of the exhaust gas varies with a change in the air-fuel ratio of a combusted air-fuel mixture. For example, when the air-fuel mixture is combusted at a stoichiometric ratio or in a fuel rich condition, most of the oxygen contained in the air-fuel mixture will be burnt out. As a result, the oxygen partial pressure of the exhaust gas becomes substantially 0. Conversely, when the air-fuel mixture is combusted in a fuel lean condition, an excess amount of oxygen is kept unburned. That is, the oxygen partial pressure of the exhaust gas becomes higher as the air-fuel ratio becomes leaner. Meanwhile, the oxygen partial pressure of the ambient air remains generally constant. Accordingly, the air-fuel ratio of the air-fuel mixture combusted in the internal combustion engine may be obtained on the basis of the output voltage of the oxygen sensor corresponding to the oxygen partial pressure relative to that of the atmosphere.

Various type of oxygen sensors may be employed as well as the aforementioned tubular oxygen sensor. The oxygen sensor including a strip-type detector, the oxygen sensor including a detector made of zirconia, or the like may be applied to the diagnosis system. The aforementioned oxygen sensor is constructed to detect an oxygen partial pressure of the exhaust gas in the same manner as described above. That is, the detector of the oxygen sensor outputs the detection signals in accordance with the difference of the oxygen partial pressure between the exhaust gas and the reference gas. Most oxygen sensors use the atmosphere as the reference gas relative to the exhaust gas in the same manner as in the oxygen sensor shown in FIG. 1.

An internal combustion engine requiring an air-fuel ratio control for the purpose only of a stoichiometric combustion tends to employ an oxygen sensor having its output voltage considerably increased or decreased at a point of the stoichiometric air-fuel ratio. The aforementioned type of oxygen sensor may satisfy the requirement of the stoichiometric combustion in spite of a low resolving power that only indicates whether the air-fuel ratio corresponding to the detected output voltage is richer or leaner than the stoichiometric air-fuel ratio. On the contrary, the internal combustion engine in which the air-fuel mixture is combusted at a wider range of the air-fuel ratio, for example, a lean-burn combustion, the oxygen sensor is required to have a relatively higher resolving power that allows the output voltage to be linearly changed in accordance with the oxygen partial pressure of the exhaust gas.

When the detector of the aforementioned oxygen sensors has a fracture as shown in FIG. 2A, the exhaust gas flows into the detector such that the inside of the detector is filled with the exhaust gas. Accordingly the oxygen partial pressures in the inside and outside of the detector become equal. The oxygen sensor becomes incapable of generating the electromotive force.

When identifying an output pattern in which detection signals indicating no difference of the oxygen partial pressure between the inside and the outside of the detector are continuously generated by monitoring the output of the oxygen sensor, it is determined that the detector is fractured.

The time period taken from the start of the output of the detection signal indicating the lean air-fuel ratio (lean signal) compared with the stoichiometric air-fuel ratio to output the signal indicating rich the air-fuel ratio (rich signal) compared with the stoichiometric air-fuel ratio is constantly measured during the engine operation. It is determined that the detector is fractured when the measured time exceeds a predetermined time period.

The aforementioned diagnosis system, however, may not always detect the fracture of the detector accurately in the case as described below. In the internal combustion engine for a vehicle, a fuel-cut control for temporarily cutting the fuel injection to the internal combustion engine is frequently performed. During the fuel-cut operation, air is supplied to the exhaust passage. As a result, both the inside and the outside of the detector are filled with air. When the fuel injection resumes in the aforementioned state, the exhaust gas resulting from combustion of the fuel may flow into the exhaust passage.

As shown in FIG. 2B, when the detector is fractured in the aforementioned state, there is substantially no difference in the oxygen partial pressure between the inside and the outside of the detector even if the air-fuel ratio becomes rich as the air-fuel combustion resumes. As a result, the oxygen sensor continues outputting the lean signal. In this state, however, a certain period of time is taken for the exhaust gas reaching the outside of the detector to enter into the inside of the detector through the fracture. Therefore, in the state immediately after the stop of the fuel-cut operation, air exists inside of the detector and the exhaust gas exists outside of the detector even if the detector is fractured. This state as indicated in FIG. 2C is similar to the state of the detector with no fracture. As a result, electromotive force is generated by the oxygen sensor caused by the difference of the oxygen partial pressure between the inside and outside of the detector. This oxygen sensor, thus, may generate the rich signal temporarily.

In the diagnosis performed on the basis of the time period for which the lean signal of the oxygen sensor is switched to the rich signal, the system may fail to detect the fracture of the detector, providing a wrong determination that the detection portion is not fractured.

In a generally employed diagnosis system disclosed in Japanese Laid-Open Patent Publication No. 8-21282, monitoring of the sensor outputs for detecting the fracture of the detector is inhibited until a predetermined time period elapses from the stop of the fuel-cut operation. As a result, the detection signal obtained immediately after the stop of the fuel-cut operation is not reflected in the abnormality diagnosis, thus avoiding diagnosis error.

Although the above-described system makes it possible to detect the fracture of the detector with a certain level of accuracy, the diagnosis system is required to be further improved.

For example, according to the abnormality diagnosis as aforementioned, monitoring of the detection signal of the oxygen sensor has to be suspended for a substantially long time period elapsing after the stop of the fuel-cut operation such that the undesirable detection signal is not reflected in the diagnosis. The long suspension of monitoring the sensor output may delay detection of the fracture of the detector, thus failing to cope with the problem caused by the abnormality of the oxygen sensor.

Depending on the operating state of the internal combustion engine, the sensor in the abnormal state owing to the fracture may take an output pattern similar to that of the oxygen sensor in the normal state with no fracture. On the contrary, the oxygen sensor in the normal state may take an output pattern similar to that of the oxygen sensor in the abnormal state. Monitoring of the sensor output for a substantially long period is required in order to distinguish the output pattern that indicates the fractured detector from the output pattern. Therefore, monitoring of the sensor outputs is required to be performed for a substantially long period of time so as to discriminate the abnormal state of the oxygen sensor from the exceptional cases.

SUMMARY OF THE INVENTION

The invention thus provides an abnormality diagnosis system and method for an oxygen sensor which accurately determines an abnormality state of an oxygen sensor owing to a fractured detector of the oxygen sensor.

According to an aspect of the invention, a diagnosis system determines an abnormality in at least one oxygen sensor including a detector interposed between a reference gas and an exhaust gas and generates a detection signal in accordance with a difference of an oxygen partial pressure between the reference gas and the exhaust gas. The diagnosis system includes a controller that determines the abnormality of the oxygen sensor owing to a fracture of the detector on the basis of an output pattern of the detection signal of the oxygen sensor. The controller then determines whether the detector has the fracture on the basis of a distribution pattern of the detection signal generated by the oxygen sensor.

As described above, when the detector is fractured, the exhaust gas enters to the inside of the detector exposed to the reference gas through the fracture. Therefore the difference of the oxygen partial pressure between the inside (reference gas) and outside (exhaust gas) of the detector becomes substantially zero. In a particular case, however, the oxygen sensor having a fractured detector may generate a detection signal indicating the difference of the oxygen partial pressure between the inside and outside of the detector in the same way as in the case where the oxygen sensor is in a normal state. Actually, however, such phenomenon is less likely to occur, and the resultant distribution of the detection signal of the oxygen sensor having the fractured detector becomes considerably different from that of the oxygen sensor in the normal state. Even if the oxygen sensor having the fractured detector generates infrequently the detection signal similar to that of the oxygen sensor in the normal state, the abnormality may be appropriately diagnosed on the basis of the distribution of the detection signal of the oxygen sensor.

According to a preferred form of the aspect of the invention, the controller determines that the detector is fractured when it is determined that a ratio of a detection signal indicating the difference of the oxygen partial pressure that is equal to or less than a first predetermined value to the detection signal of the oxygen sensor becomes equal to or greater than a second predetermined value.

As described above, the oxygen sensor having the fractured detector may infrequently generate the detection signal indicating the difference of the oxygen partial pressure between the inside and the outside of the detector. The ratio of the detection signal indicating the difference of the oxygen partial pressure to the detection signal, however, is small. As the distribution of the detection signal of the oxygen sensor having the fractured detector takes a pattern in which distribution of the detection signal concentrates in the region indicating the relatively small difference of the oxygen partial pressure between the inside and outside of the detector. Accordingly, it can be determined that the detector is fractured when the ratio of detection signal indicating the relatively small difference of the oxygen partial pressure to the detection signal is larger than a predetermined value.

According to another preferred form of the aspect of the invention, the controller determines that the detector is not fractured when it is determined that a ratio of a detection signal indicating the difference of the oxygen partial pressure that is equal to or greater than a third predetermined value to the detection signal of the oxygen sensor becomes equal to or greater than a fourth predetermined value.

When the detector is not fractured, distribution of the frequency in generating the detection signal of the oxygen sensor does not concentrate in the region indicating small difference of the oxygen partial pressure. Accordingly, it can be determined that the detector is not fractured when the ratio of detection signal indicating a relatively large difference in the oxygen partial pressure to the detection signal is larger than a predetermined value.

According to another aspect of the invention, a diagnosis system determines an abnormality in at least one oxygen sensor being provided downstream of a catalyst of an exhaust system in an internal combustion engine. The oxygen sensor includes a detector interposed between an atmosphere and an exhaust gas, and generates a detection signal in accordance with a difference of an oxygen partial pressure between the atmosphere and the exhaust gas. The diagnosis system includes a controller that determines the abnormality of the oxygen sensor owing to a fracture of the detector on the basis of an output pattern of the detection signal of the oxygen sensor. The controller inhibits the detection signal of the oxygen sensor from being used for determining the abnormality of the oxygen sensor until a predetermined period of time elapses from a point of time when a fuel-cut operation of the internal combustion engine is stopped, calculates a quantity of oxygen absorbed by the catalyst during the fuel-cut operation, and sets the predetermined period of time to a value that changes depending upon the calculated quantity of oxygen absorbed by the catalyst.

When the oxygen partial pressure of the inside of the detector is increased by a fuel-cut operation, the catalyst starts absorbing. The absorbed oxygen is gradually released into the exhaust gas as the oxygen partial pressure of the outside of the detector (exhaust gas) decreases immediately after stop of the fuel-cut operation. As a result, the oxygen partial pressure of the outside of the detector (exhaust gas) is kept high for a predetermined time period after the stop of the fuel-cut operation. Therefore, it is necessary to inhibit the detection signals of the oxygen sensor generated for the predetermined time period after the stop of the fuel-cut operation from being reflected in the abnormality diagnosis such that the diagnosis is accurately performed on the basis of the output pattern of the oxygen sensor.

The time period for which the high oxygen partial pressure state is kept after the stop of the fuel-cut operation changes depending on the quantity of oxygen absorbed in the catalyst during the fuel-cut operation. The time period for which the generated detection signal is inhibited from being reflected in the abnormality diagnosis is set on the basis of the quantity of oxygen absorbed in the catalyst during the fuel-cut operation. The diagnosis error caused by the state where the oxygen is released from the catalyst immediately after the stop of the fuel-cut operation may be effectively avoided while keeping opportunities for performing the abnormality diagnosis from being reduced.

According to another aspect of the invention, a diagnosis system determines an abnormality in at least one oxygen sensor being provided downstream of a catalyst of an exhaust system in an internal combustion engine. The oxygen sensor includes a detector that isolates an atmosphere from an exhaust gas, and generates a detection signal. The diagnosis system includes a controller that determines the abnormality of the oxygen sensor owing to a fracture of the detector on the basis of an output pattern of the detection signal of the oxygen sensor. The controller inhibits the detection signal of the oxygen sensor from being used for determining the abnormality of the oxygen sensor until a predetermined period of time elapses from a point of time when a fuel-cut operation of the internal combustion engine is stopped, and sets the predetermined period of time in accordance with at least one of a total value of an intake air quantity during the fuel-cut operation and a catalyst temperature.

The more the quantity of air is fed into the exhaust system of the engine during the fuel-cut operation, the more the quantity of oxygen absorbed in the catalyst becomes during the fuel-cut operation. The air quantity can be derived from the total value of the intake air quantity during the fuel-cut operation. As the oxygen absorbing capacity of the catalyst varies depending on the temperature, the quantity of oxygen absorbed in the catalyst during the fuel-cut operation varies accordingly. In the diagnosis system, the time period for which the detection signal of the oxygen sensor is inhibited from being reflected in the abnormality diagnosis is set to a value that changes in accordance with the total intake air quantity during the fuel-cut operation and the catalyst temperature. The resultant time period, thus, can be minimized so as to avoid the diagnosis error.

According to another aspect of the invention, a diagnosis system determines an abnormality in at least one oxygen sensor including at least one detector that isolates a reference gas from an exhaust gas and generates a detection signal in accordance with a difference of an oxygen partial pressure between the reference gas and the exhaust gas. The diagnosis system includes a controller that determines the abnormality of the oxygen sensor owing to a fracture of the detector on the basis of an output pattern of the detection signal of the oxygen sensor. The controller detects a temperature of the detector and inhibits the detection signal of the oxygen sensor from being used for determining the abnormality of the oxygen sensor when the detected temperature is lower than an activating temperature of the detector.

When the temperature of the detector has not reached the activation temperature, the oxygen sensor may fail to generate an accurate detection signal in accordance with the operation state of the internal combustion engine. In some cases, the oxygen sensor having no fractured detector may generate a similar detection signal to that normally obtained when the detector is fractured. In the aforementioned diagnosis system, the detecting signal generated by the oxygen sensor is inhibited from being reflected in the abnormality diagnosis until the temperature of the detector reaches the activation temperature. The diagnosis error owing to the temperature of the detector as described above can be effectively avoided.

According to another aspect of the invention, a diagnosis system determines an abnormality in at least one oxygen sensor including one detector interposed between an atmosphere and an exhaust gas and that generates a detection signal in accordance with a difference of an oxygen partial pressure between the atmosphere and the exhaust gas. The diagnosis system includes a controller that determines the abnormality of the oxygen sensor owing to a fracture of the detector on the basis of an output pattern of the detection signal of the oxygen sensor. The controller determines that the detector is fractured upon generation of the detection signal of the oxygen sensor, which indicates that the oxygen partial pressure of the exhaust gas is higher than that of the air.

The oxygen partial pressure of the combusted exhaust gas never becomes higher than that of the air under no circumstances even if the fuel-cut operation is performed. The oxygen sensor, in some cases, may generate the detection signal indicating that the oxygen partial pressure of the exhaust gas is higher than that of air depending on the operating state of the engine. Accordingly, the fracture of the detector can be easily and accurately determined on the basis of the detection signal which is not expected to be generated by the oxygen sensor in the normal state.

BRIEF DESCRIPTION OF THE DRAWINGS

The foregoing and further objects, features and advantages of the invention will become apparent from the following description of preferred exemplary embodiments with reference to the accompanying drawings, wherein like numerals are used to represent like elements and wherein:

FIGS. 5A–4C are graphs each showing the distribution pattern of the output voltage of the oxygen sensor when the oxygen sensor is in the normal state during the engine operation, the oxygen sensor is in the normal state during the high load engine operation, and the oxygen sensor is in the abnormal state, respectively;

FIGS. 6A–6C are graphs each showing another distribution pattern of the output voltage of the oxygen sensor when the oxygen sensor is in the normal state during the engine operation, the oxygen sensor is in the normal state during the high load engine operation, and the oxygen sensor is in the abnormal state, respectively;

DETAILED DESCRIPTION OF PREFERRED EMBODIMENTS

First Exemplary Embodiment

A first exemplary embodiment will be described in detail with reference to FIG. 3 through FIG. 7.

Figure 3:
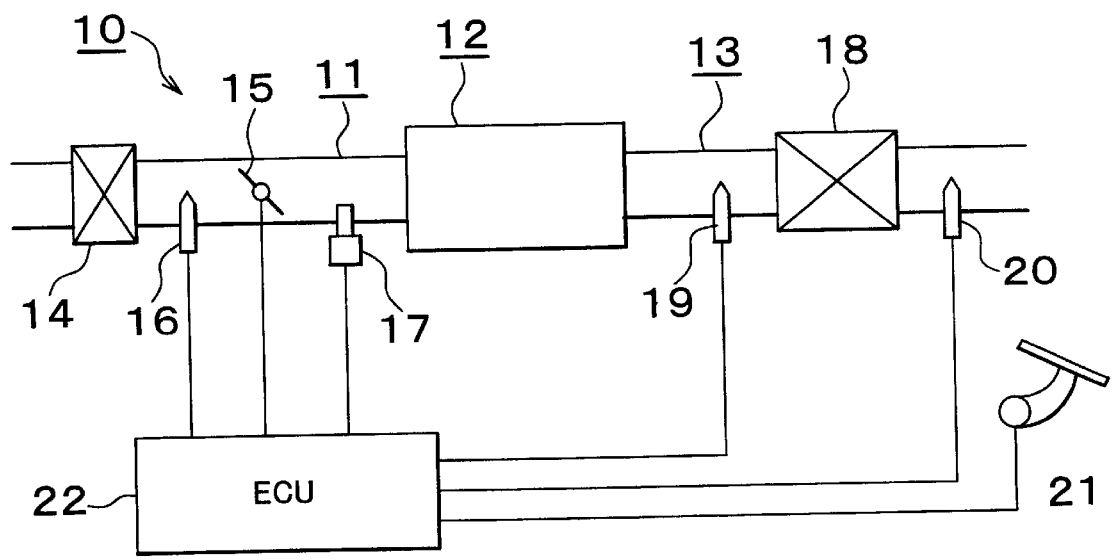
FIG. 3 is a schematic drawing showing a construction of an exhaust purification system including an abnormality diagnosis system.

First, a construction of an exhaust purification system for an internal combustion engine of a vehicle, including an abnormality diagnosis system according to the invention, will be described. Referring to FIG. 3, a throttle valve 15 is disposed in an intake air passage 11 of an internal combustion engine 10. The throttle valve 15 is controlled to change a sectional area of the intake air passage 11, to adjust a quantity of air (intake air quantity) flowing through the intake air passage 11 via an air cleaner 14. The intake air quantity is detected by an airflow meter 16. The air flowing through the intake air passage 11 is mixed with the fuel injected from an injector 17 disposed downstream of the throttle valve 15 and is delivered into a combustion chamber 12 to be combusted therein.

Meanwhile, the exhaust gas generated in the combustion of the air-fuel mixture in the combustion chamber 12 flows through an exhaust passage 13. In the exhaust passage 13, a three-way catalyst 18 for purifying harmful substances contained in the exhaust gas is disposed. Further, a front oxygen sensor 19 is disposed upstream of the three-way catalyst 18 whereas a rear oxygen sensor 20 is disposed downstream thereof.

The three-way catalyst 18 performs an effective purification of major harmful substance (HC, CO, NOx) only when the air-fuel ratio of the air-fuel mixture is within a narrow window in the vicinity of the stoichiometric air-fuel ratio. For effectively purifying the exhaust gas by the three-way catalyst 18, therefore, it is necessary to accurately control the air-fuel ratio of the air-fuel mixture to be brought into a center of the window as aforementioned.

Such a strict control of the air-fuel ratio is performed by an electronic control unit (ECU) 22. The ECU 22 receives detection signals of various sensors including the airflow meter 16, the oxygen sensors 19 and 20, an accelerator sensor 21 for detecting a depression amount of an accelerator pedal, and an NE sensor (not shown in the figure) for detecting an engine speed. According to operation states of the internal combustion engine 10, vehicle, and the like, the ECU 22 performs an air-fuel ratio control as described above, by controlling the throttle valve 15, injector 17 and the like. Hereinafter, such an air-fuel ratio control by the ECU 22 will be described.

The ECU 22 calculates the required intake air quantity in accordance with detected values of the depression amount of the accelerator pedal, engine speed and the like and adjusts the opening of the throttle valve 15 so as to obtain the calculated required intake air quantity. Meanwhile the ECU 22 calculates the fuel quantity required to achieve the stoichiometric air-fuel ratio in accordance with an actual intake air quantity detected by the airflow meter 16, and adjusts the quantity of the fuel to be injected by the injector 17. The aforementioned control may bring the air-fuel ratio of the air-fuel mixture to be combusted in the combustion chamber 12 to the value close to the stoichiometric ratio to a certain extent. The control, however, is not sufficient for the required air-fuel ratio control.

The ECU 22, therefore, further carries out a feedback correction of the fuel injection quantity of the injector 17 on the basis of the actual air-fuel ratio derived from the detected values of the oxygen sensors 19 and 20, thus attaining the required high accuracy in the air-fuel ratio control.

As described above, the exhaust gas purification system performs the feedback correction of the fuel injection quantity of the injector 17 according to the detected values of the oxygen sensors 19 and 20, which may be called an air-fuel ratio feedback control. The air-fuel ratio feedback control maintains the air-fuel ratio of the air-fuel mixture in the vicinity of the stoichiometric air-fuel ratio so as to attain a high exhaust gas purification rate. In particular, according to the above-described exhaust purification system, a further improvement is made in the air-fuel ratio control accuracy by detecting oxygen partial pressures upstream and downstream of the three-way catalyst 18 by the oxygen sensors 19 and 20, respectively.

Figure 1:
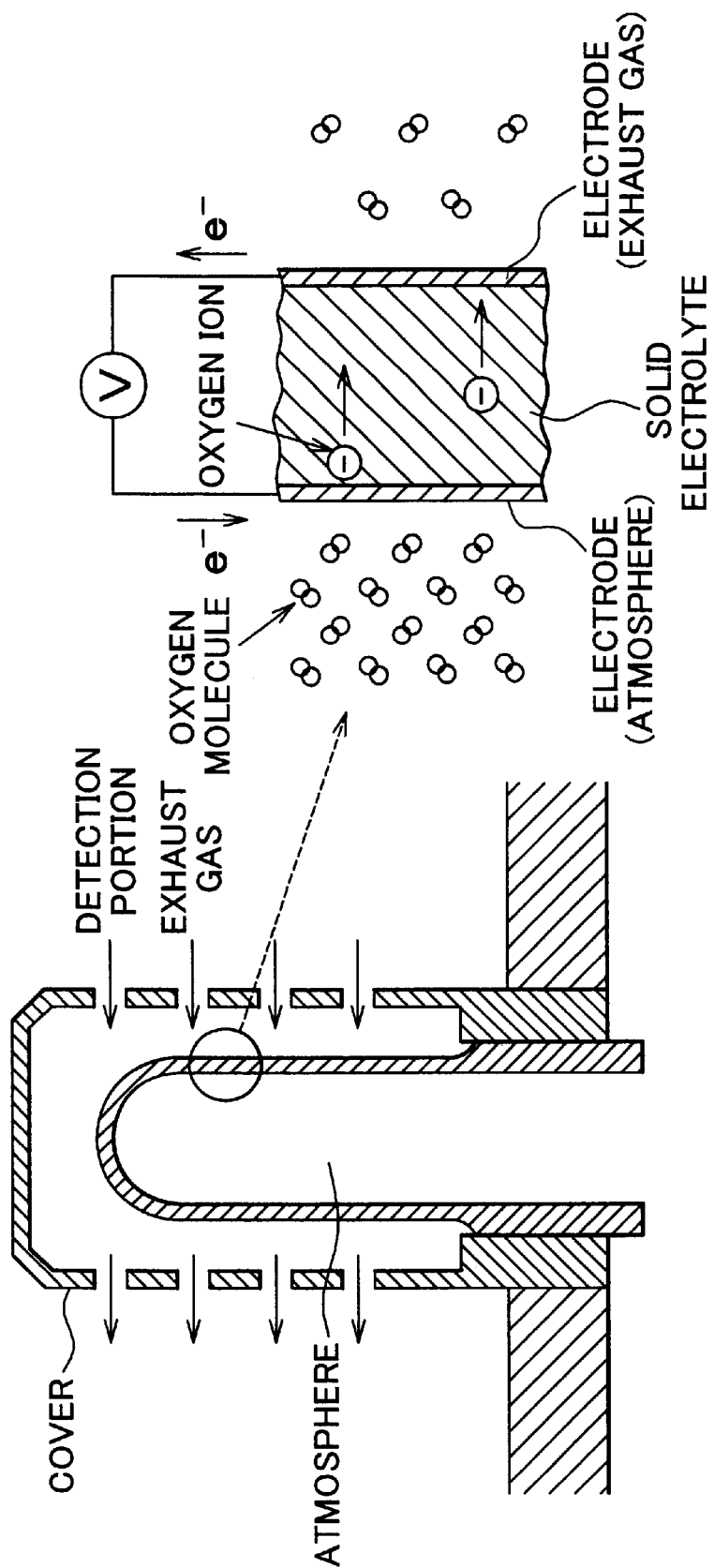
FIG. 1 shows a schematic view representing an oxygen sensor.
Figure 2A:
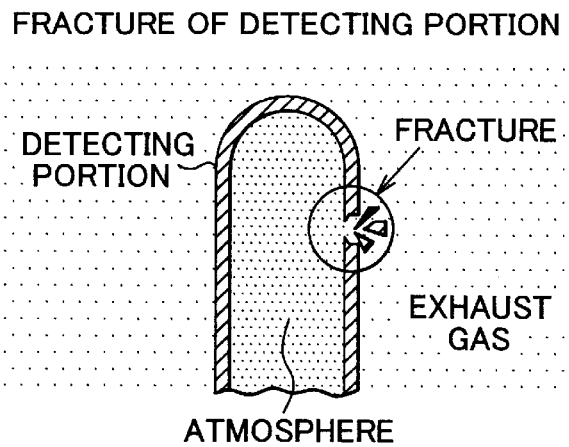
FIGS. 2A to 2C show the respective states in which a fracture is caused in a detector of the oxygen sensor, there is substantially no difference of the oxygen partial pressure between the inside and outside of the detector, and there is the difference of the oxygen partial pressure of the exhaust gas between an inside/outside of the detector.
Figure 2B:
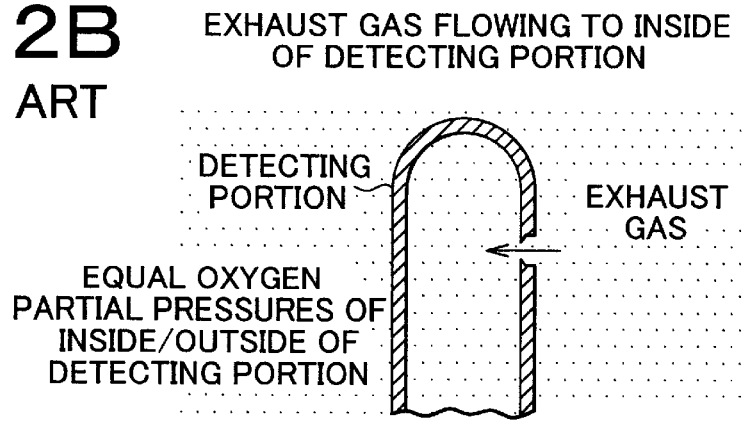
Figure 2C:
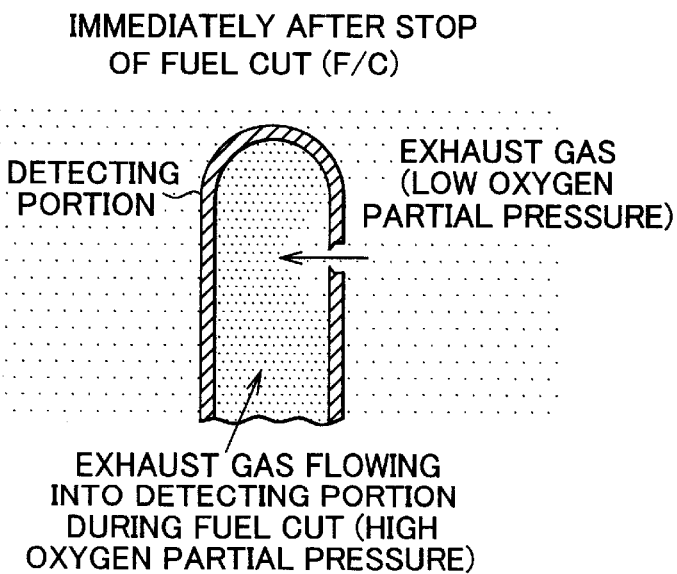

The oxygen sensors 19 and 20 employed in the exhaust purification system are both constructed as shown in FIG. 1, including a detector which isolates the atmosphere and the exhaust gas, and generates voltage corresponding to the difference in the oxygen partial pressure.

Figure 4:
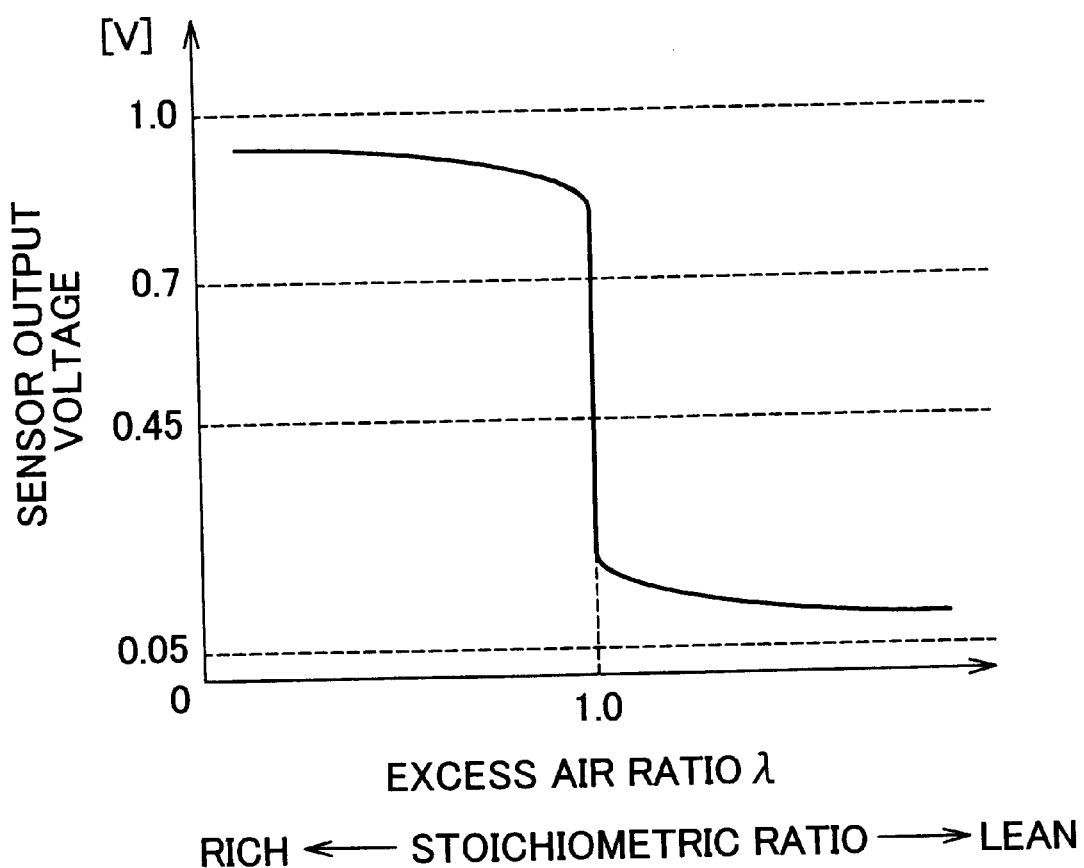
FIG. 4 is a graph showing an example of output pattern of the oxygen sensor.

FIG. 4 shows an output characteristic of the oxygen sensors 19, 20. Referring to FIG. 4, "excess air ratio 1" represents a weight ratio of air to the air-fuel mixture at the stoichiometric air-fuel ratio (1=1.0)(1=[air weight]/[air-fuel mixture weight]/[weight ratio of air to air-fuel mixture at the stoichiometric air-fuel ratio])

As shown in FIG. 4, the output voltage of the oxygen sensors 19, 20 sharply change at a threshold value of the excess air-fuel ratio 1 of 1.0. When the air-fuel ratio is leaner than the stoichiometric air-fuel ratio (1>1.0), the output voltage sharply decreases to be relatively low. When the air-fuel ratio is richer than the stoichiometric air-fuel ratio (1<1.0), the output voltage sharply increases to be relatively high. Here, the threshold value of the output voltage is set to 0.45 V, which is used to determine whether the voltage detected by the oxygen sensor 19 or 20 is richer or leaner than the stoichiometric air-fuel ratio. The voltage detected by the oxygen sensor 19 or 20 changes depending on the temperature of the detector. However, the oxygen sensor is designed such that the tendency of the oxygen sensor, which is likely to sharply change the voltage detected by the oxygen sensor at the stoichiometric air-fuel ratio, is constantly held.

FIG. 5A through FIG. 5C show examples of output patterns of the rear oxygen sensor 20 during the operation of the internal combustion engine 10. FIG. 5A shows an example of an output pattern of the rear oxygen sensor 20 in its normal state, which is obtained when the engine combustion is performed at the stoichiometric air-fuel ratio while implementing the air-fuel ratio feedback control. As shown in FIG. 5A, during the engine combustion at the stoichiometric air-fuel ratio, the output voltage of the rear oxygen sensor 20 in its normal state takes a pattern in which a high voltage indicating a richer air-fuel ratio compared with the stoichiometric air-fuel ratio and a low voltage indicating a leaner air-fuel ratio compared with the stoihciometric air-fuel ratio repeat alternately.

Next, when the internal combustion engine 10 operates at a high load, the air-fuel mixture is combusted at a richer air-fuel ratio compared with the stoichiometric air-fuel ratio. In this case, the output voltage takes a pattern in which the voltage is held at a relatively high voltage range indicating richer air-fuel ratio compared with the stoichiometric air-fuel ratio as shown in FIG. 5B.

The output voltage of the oxygen sensor having a fractured detector takes a pattern as shown in FIG. 5C. When the detector is fractured, the output voltage is kept at substantially "0" V indicating that the difference of the oxygen partial pressure between the exhaust gas and the atmosphere is almost 0. This pattern, however, may occasionally show the high voltage depending on a sharp change in the output of the oxygen sensor, for example, after a stop of the fuel-cut operation. As described above, the output pattern of the oxygen sensor in an abnormal state, that is, fractured detector, is significantly different from the output pattern of the oxygen sensor 20 in the normal state.

FIG. 6A through FIG. 6C show frequency distributions of the oxygen sensor 20 relative to the output patterns shown in FIG. 5A through FIG. 5C, respectively. As shown in FIG. 6C, the frequency distribution of output of the oxygen sensor 20 having a fractured detector shows that generation of the output voltage concentrates in a low voltage region where the air-fuel ratio is leaner compared with the stoichiometric air-fuel ratio. Therefore such distribution can be clearly distinguished from those of the output voltage of the oxygen sensor 20 in the normal state as shown in FIG. 6A and FIG. 6B. Accordingly, it is possible to easily determine a fracture in the detector by referring to such frequency distributions of the output voltages of the oxygen sensors 19 and 20.

In the exemplary embodiment, therefore, the frequency distribution of an output voltage of the oxygen sensor 20 is obtained by monitoring the sensor output during the engine operation. On the basis of the resultant frequency distribution, the abnormality diagnosis for determining a fracture of the detector is carried out. A control routine for implementing the abnormality diagnosis will be described in detail referring to FIG. 7.

Figure 7:
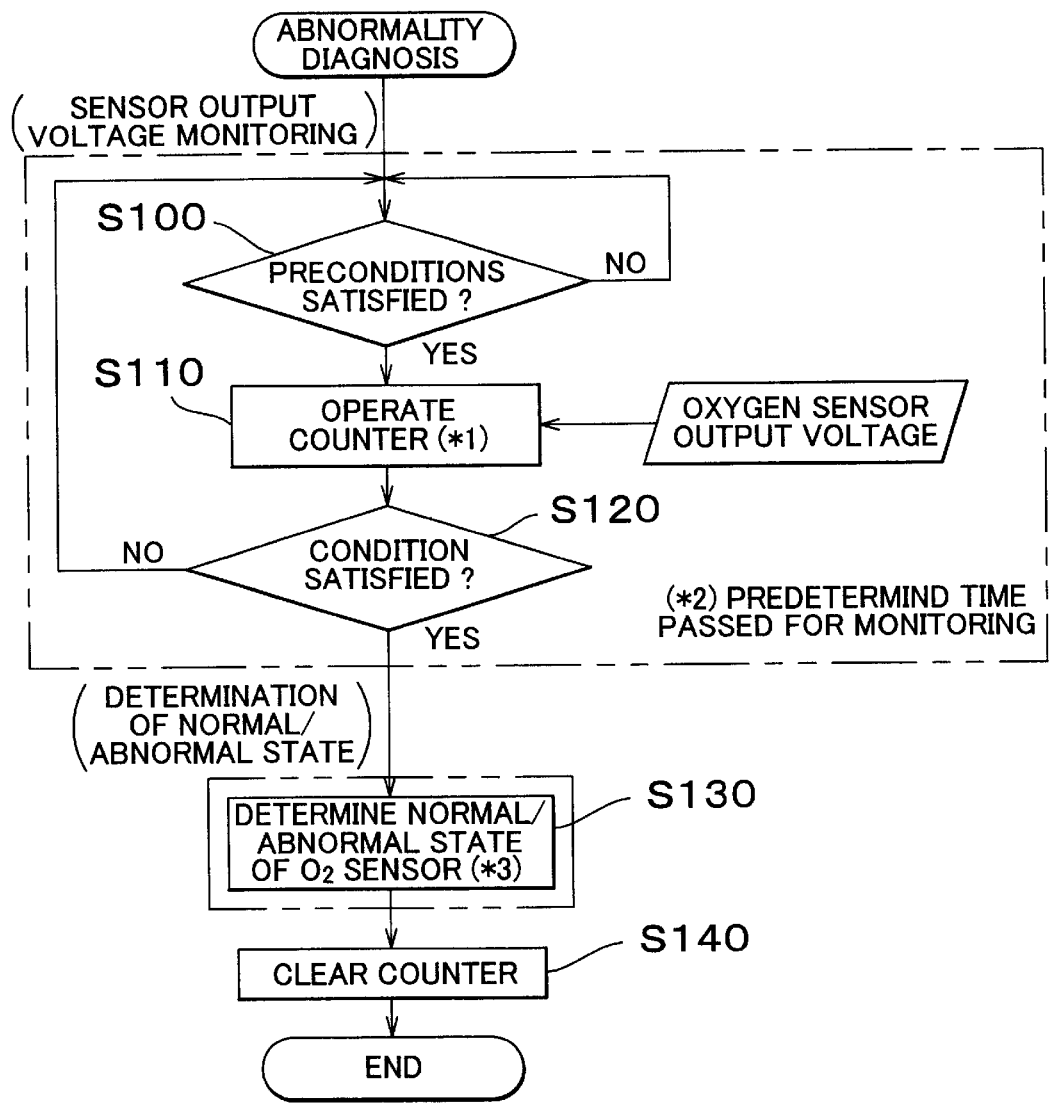
FIG. 7 is a flowchart showing a control routine of the abnormality diagnosis in an exemplary embodiment of the invention.

FIG. 7 is a flowchart showing a control routine for implementing the abnormality diagnosis. This routine is repeatedly implemented by the ECU 22 for the rear oxygen sensor 20 that is disposed downstream of the three-way catalyst 18 during the engine operation.

In the abnormality diagnosis, the output voltage of the rear oxygen sensor 20 is monitored for a predetermined time period such that the frequency of output of the oxygen sensor 20 is obtained. The output voltage of the oxygen sensor 20 is monitored as described below.

In the routine shown FIG. 7, the ECU 22 continues to perform the abnormality diagnosis so long as YES is obtained in step S100, that is, so long as the precondition for performing the diagnosis is established. In the exemplary embodiment, the precondition is established by satisfying the following conditions:

(c1) The vehicle speed is equal to or higher than a predetermined speed K8;

(c2) An idling operation is not being performed;

(c3) The fuel-cut operation is not being performed; and (c4) The intake air quantity is equal to or greater than a predetermined quantity K9.

Establishment of the aforementioned precondition allows the rear oxygen sensor 20 to generate the voltage resulting from sufficient difference of the oxygen partial pressure between the exhaust gas and the atmosphere owing to a large quantity of air-fuel mixture to be combusted such that the abnormality diagnosis is implemented.

So long as YES is obtained in step S100, that is, the precondition is satisfied, the ECU 22 repeatedly carries out sampling of the output voltage of the rear oxygen sensor 20 at predetermined intervals.

In the first exemplary embodiment, the output voltage signals of the rear oxygen sensor 20 are distributed in four regions (A), (B), (C), and (D) as described below:

Region (A): a region in which almost no voltage is generated by the rear oxygen sensor 20 (0.05V or lower);

Region (B): a region in which the voltage is generated by the rear oxygen sensor 20 in the normal state when the air-fuel ratio of the air-fuel mixture is lean compared with the stoichiometric air-fuel ratio (0.05–0.45V);

Region (C): a region between the Regions (B) and (D) in which the voltage generated by the rear oxygen sensor 20 ranges from 0.45–0.7 V; and Region (D): a region in which the voltage is generated by the rear oxygen sensor 20 in the normal state when the air-fuel ratio of the air-fuel mixture is rich compared with the stoichiometric air-fuel ratio (0.7 V or higher).

The ECU 22 stores output frequencies in the respective regions (A) through (D) by incrementing counters Ca, Cb, Cc, and Cd corresponding to the respective regions at every sampling of the output voltage in step S110.

The above-described sampling and incrementing of the counters are repeatedly carried out until NO is obtained in step S100, that is, the precondition becomes unsatisfied, or until YES is obtained in step S120, that is, a determination condition is satisfied. The determination condition is satisfied when a predetermined time period elapses from monitoring performed upon start of the sampling.

When NO is obtained in step S100, that is, the precondition becomes unsatisfied during monitoring of the output voltage of the rear sensor 20, the values of the counters Ca, Cb, Cc, and Cd are respectively reserved. When the precondition is satisfied again, the abnormality diagnosis is restarted.

When YES is obtained in step S120, that is, the determination condition is satisfied, and the sampling of the output voltage is completed, the process proceeds to step S130. In step S130, it is determined whether the rear oxygen sensor 20 is operated in normal state or abnormal state on the basis of the monitoring results.

Referring to FIG. 6C, when the detector of the rear oxygen sensor 20 is fractured, the obtained output voltage is mainly distributed in the low voltage regions (A) and (B), in which relatively low voltage is generated by the oxygen sensor in the normal state, indicating that the air-fuel ratio of the air-fuel mixture is leaner than the stoichiometric air-fuel ratio. There is a certain frequency of the sensor output in the high voltage region (C) and (D) indicating that the air-fuel ratio of the air-fuel mixture is richer than the stoichiometric air-fuel ratio.

In the embodiment, it is determined that the detector is not fractured and, therefore, the rear oxygen sensor 20 is in the normal state when at least one of the following conditions is satisfied:

(a1) The value of the counter Cd is equal to or greater than a predetermined value K1. That is, the output frequency of the rear oxygen sensor 20 distributed in the region (D) during the monitoring period is equal to or greater than a predetemrined value K1; and (a2) The sum of the values of the counters Cc and Cd is equal to or greater than a predetermined value K2. That is, the output frequency of the rear oxygen sensor 20 distributed in the regions (C) and (D) is equal to or greater than a predetermined value.

Meanwhile, it is determined that the detector is fractured and, therefore, the rear oxygen sensor 20 is in the abnormal state, when the following conditions are all satisfied:

(b1) The value of the counter Ca is equal to or greater than a predetermined value K4. That is, the output frequency of the rear oxygen sensor 20 distributed in the region (A) during the monitoring period is equal to or greater than a predetermined value;

(b2) The value of the counter Cd is smaller than a predetermined value K5. That is, the output frequency of the rear oxygen sensor 20 distributed in the region (D) during the monitoring period is smaller than a predetermined value; and (b3) The sum of the values of the counters Cc and Cd is smaller than a predetermined value K6. That is, the output frequency of the rear oxygen sensor 20 distributed in the regions (C) and (D) is smaller than a predetermined value.

After completion of the normality/abnormality determination implemented in step S130, the process proceeds to step S140. In step S140, all values of the counters are cleared and the process ends. When the normality/abnormality determination is unsuccessful, the abnormality diagnosis is restarted upon establishment of the precondition.

The abnormality diagnosis on the basis of the output frequency of the oxygen sensor 20 distributed in the respective voltage regions allows accurate detection of the fracture of the detector even when the oxygen sensor 20 having a fractured detector temporarily generates a high voltage signal owing to the abrupt change in the oxygen partial pressure of the exhaust gas after stop of the fuel-cut operation.

As described above, when the detector is fractured, the rear oxygen sensor 20 may temporarily generate a high voltage signal caused by the abrupt change in the oxygen partial pressure of the exhaust gas. Generation of the high voltage signal does not continue long but ends within a short period of time. In the exemplary embodiment, accordingly, the ECU 22 measures the time period for which the rear oxygen sensor 20 continues generating a voltage (0.45V or higher) indicating a rich air-fuel ratio of the air-fuel mixture compared with the stoichiometric air-fuel ratio during the monitoring. This may allow the ECU 22 to determine that the detector of the rear oxygen sensor 20 is not fractured even when the maximum value of the measured time is equal to or greater than a predetermined value.

In the first exemplary embodiment, the above-described abnormality diagnosis may be carried out with respect to the front oxygen sensor 19 disposed upstream of the catalyst 18 instead of the rear oxygen sensor 20.

In this exemplary embodiment, the abnormality diagnosis for determining a fracture in the detector is carried out based on the output frequency of the rear oxygen sensor 20 distributed in the respective voltage regions. Therefore, even when the rear oxygen sensor 20 having a fractured detector temporarily generates a high voltage, the fracture of the detector can be accurately detected.

Second Exemplary Embodiment

A second exemplary embodiment of the invention will be described referring to FIG. 8 and FIG. 9, focusing on the features different from that of the first exemplary embodiment.

A fracture of the detector may be detected on the basis of the output pattern of the oxygen sensor, for example, the output frequency of the oxygen sensor distributed in the respective voltage regions, or the time period for which the lean signal of the oxygen sensor is continuously generated. In particular cases, however, the oxygen sensor having a fractured detector may take a similar output pattern to that derived from an oxygen sensor in the normal state. On the contrary, the oxygen sensor in the normal state may take a similar output pattern to that derived from an oxygen sensor having a fractured detector. In the cases as described below, the oxygen sensor may generate a misleading sensor output pattern especially in the cases as described below.

(Case 1) Immediately after the Stop of the Fuel-Cut Operation:

When the internal combustion engine 10 is operating during the fuel-cut operation, air flows in the exhaust passage 13. At this time, a part of the oxygen contained in the air is absorbed in the three-way catalyst 18. When the fuel-cut operation is finished and the fuel injection is resumed, the oxygen partial pressure in the exhaust gas starts decreasing. Then the catalyst 18 starts gradually releasing the oxygen absorbed therein. For a predetermined period after the stop of the fuel-cut operation, therefore, the oxygen partial pressure in the exhaust passage 13 downstream of the catalyst 18 remains high due to the thus released oxygen and the difference in the oxygen partial pressure between the atmosphere and the exhaust gas remains small. It may happen that the rear oxygen sensor 20 in the normal state, disposed downstream of the catalyst 18, takes a similar output pattern to that derived from the oxygen sensor having a fractured detector.

(Case 2) Detector at a Low Temperature:

Generally, an element used for forming a detector of an oxygen sensor such as a solid electrolyte is not capable of generating a sufficiently high voltage until the temperature of the solid electrolyte is increased for activation. In the aforementioned state of the detector at the temperature lower than the activation temperature, the voltage generated by the oxygen sensor may decrease even if the oxygen sensor has no fractured detector. As a result, substantially no rich signal is generated by the oxygen sensor. Therefore, when the temperature of the detector is low, the oxygen sensor in the normal state may take the output pattern similar to that derived from the oxygen sensor having the fractured detector.

In the aforementioned cases 1 and 2, the oxygen sensor in the normal state may take the output pattern similar to that derived from the oxygen sensor in the abnormal state at a time immediately after the stop of the fuel-cut operation or when the detector temperature is low. This may prevent appropriate diagnosis of the fracture in the detector.

In this exemplary embodiment, the temperature of the detector of the oxygen sensor 20 is monitored for the abnormality diagnosis. If the detector temperature is not sufficiently increased, the monitoring of the output voltage of the oxygen sensor 20 is inhibited so as not to be reflected in the abnormality diagnosis.

According to the diagnosis system disclosed in JP-A-8-21282, monitoring of the output pattern of the oxygen sensor for the abnormality diagnosis is inhibited for a predetermined time period after the stop of the fuel-cut operation so as to avoid the abnormality diagnosis error caused by the increase in the oxygen partial pressure of the exhaust gas in the vicinity of the oxygen sensor owing to the release of the oxygen from the catalyst 18. However, the abnormality diagnosis is stopped while monitoring is inhibited. This may reduce opportunities of implementing the abnormality diagnosis.

The time period for which the oxygen partial pressure of the exhaust gas is held high after the stop of the fuel-cut operation, that is, the period taken for sufficient release of the oxygen that has been absorbed in the catalyst 18, changes depending on the quantity of the oxygen absorbed in the catalyst 18. The monitoring inhibition period is set to a minimum value on the basis of the oxygen quantity absorbed in the catalyst 18 during the fuel-cut operation so as to avoid deterioration in the diagnosis accuracy caused by increased oxygen partial pressure of the exhaust gas owing to the release of the oxygen from the catalyst 18.

The quantity of oxygen absorbed in the catalyst 18 during the fuel-cut operation is obtained in the following manner. The larger the quantity of air fed into the exhaust passage 13 is increased, the more the quantity of oxygen is absorbed in the catalyst 18. The air quantity is obtained by a total value of the quantity of the intake air during the fuel-cut operation. Meanwhile, activation state of the catalyst 18 changes depending on the temperature, and accordingly, the oxygen absorbing capability of the catalyst 18 during the fuel-cut operation changes. As a result, the oxygen absorbing quantity of the catalyst 18 during the fuel-cut operation can be obtained as a function of the total value of the intake air quantity during the fuel-cut operation and a function of the temperature of the catalyst 18.

In the second exemplary embodiment, reduction of the opportunity for implementing the abnormality diagnosis is restrained by setting the monitoring inhibiting period in accordance with the thus obtained quantity of absorbed oxygen, and inhibiting the monitoring of the voltage generated by the oxygen sensor for a predetermined time period after stop of the fuel-cut operation.

Figure 8:
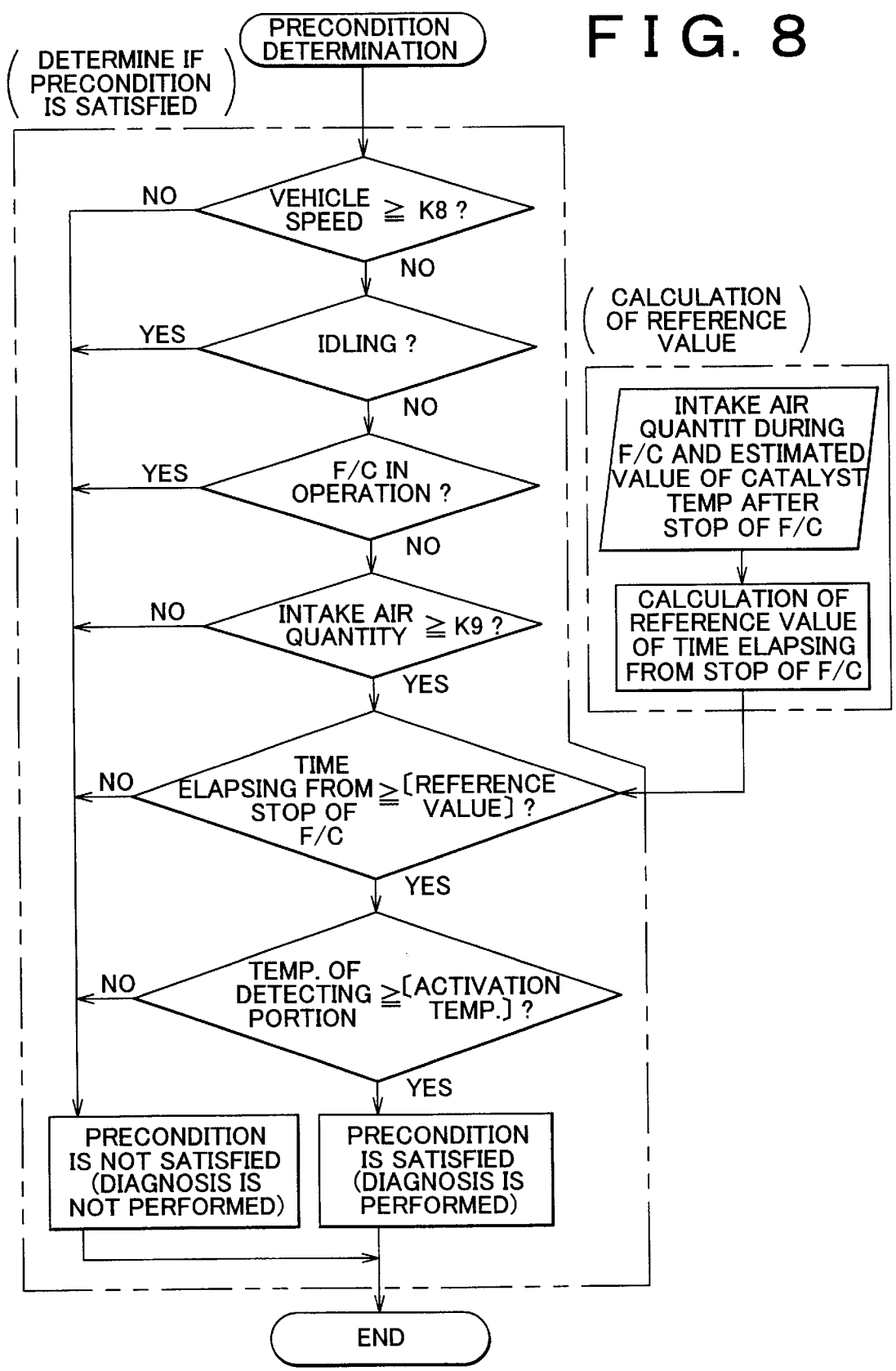
FIG. 8 is a flowchart showing a control routine for determining if establishment of the preconditions for performing the abnormality diagnosis in another exemplary embodiment of the invention.
Figure 9:
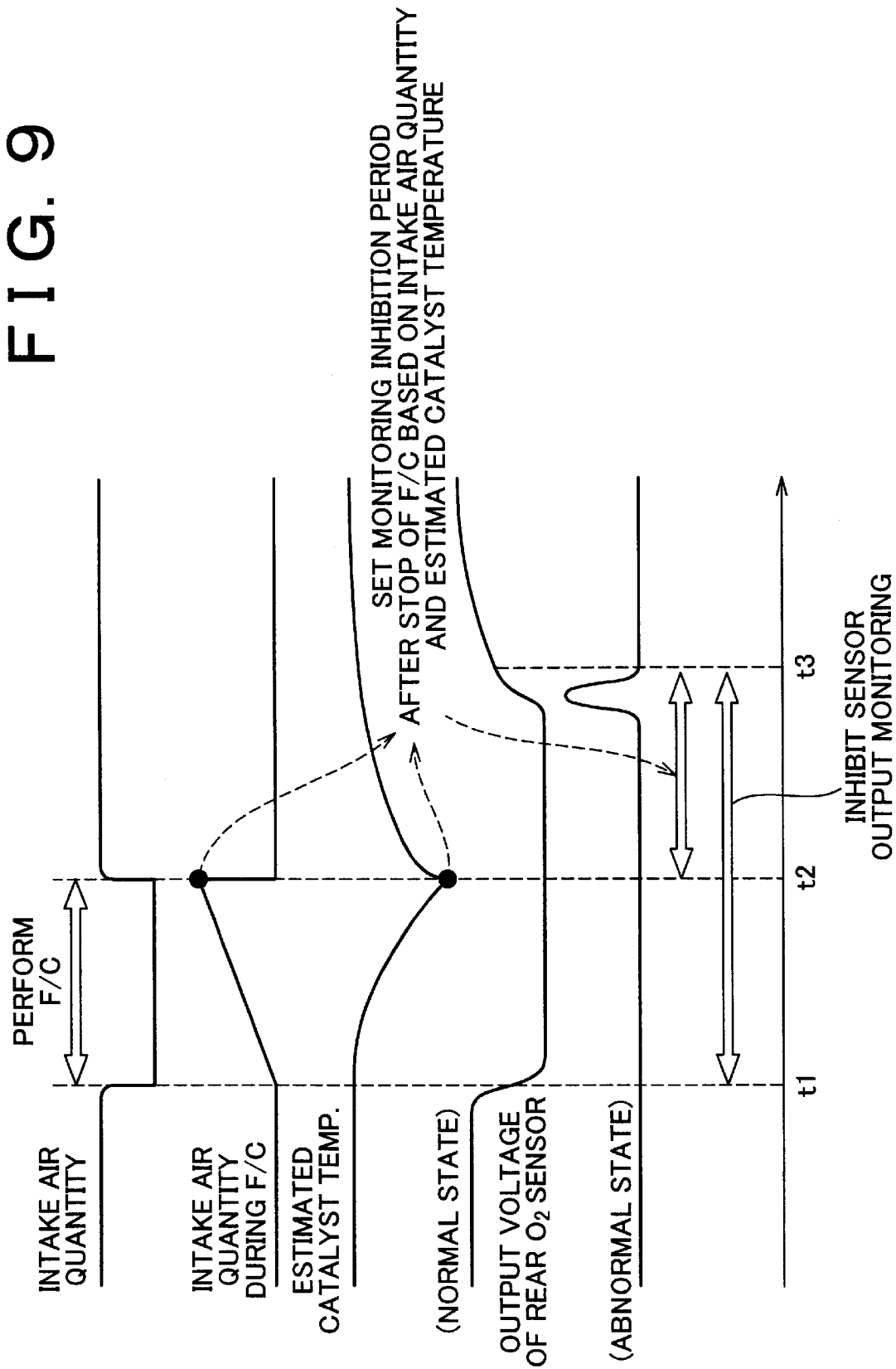
FIG. 9 is a timing chart showing change in the respective values based on which the diagnosis is performed.

FIG. 8 shows a control routine executed by the ECU 22 for determining whether the precondition for the abnormality diagnosis is established. In this control routine, it is determined that the monitoring of the output voltage of the oxygen sensor for the abnormality diagnosis is performed. When it is determined that the precondition is not established, the ECU 22 stops the abnormality diagnosis, and resumes the diagnosis upon establishment of the precondition.

As shown in FIG. 8, the abnormality diagnosis is implemented when the following conditions (c1)–(c6) are all satisfied:

(c1) The vehicle speed is equal to or higher than a predetermined value K8;

(c2) The idling operation is not being performed;

(c3) The fuel-cut operation is not being performed;

(c4) The intake air quantity is equal to or larger than a predetermined value K9;

(c5) The time elapsing from the stop of the fuel-cut operation is equal to or longer than a predetermined time (time elapsed>[reference value]); and (c6) The temperature of the detector is equal to or higher than the activation temperature thereof.

The conditions (c1) through (c4) are common with those of the first exemplary embodiment, and (c5) and (c6) are newly added conditions.

The reference value in the condition (c5) is calculated based on the total intake air quantity during the fuel-cut operation and an estimated value of the catalyst temperature. More specifically, the ECU 22 calculates the reference value using a map stored in a memory of the ECU 22. This map contains the reference values as appropriate values in accordance with the total intake air quantity during the fuel-cut operation and the estimated value of the catalyst temperature with respect to the time required for sufficiently reducing the influence of the release of the oxygen from the catalyst 18 after the stop of the fuel-cut operation to the abnormal diagnosis. The aforementioned appropriate value can be preliminarily obtained by implementing experiments.

Further, the catalyst temperature changes depending on the temperature and flow rate of the exhaust gas flowing through the catalyst 18. For example, in the case where a large quantity of high-temperature exhaust gas continuously flows in the exhaust passage 13 such as when the engine is operating at a high load, the catalyst temperature becomes high. Conversely, in the case where a small quantity of low-temperature exhaust gas continuously flows in the exhaust passage 13, such as when the engine is operating at a low load, the catalyst temperature becomes low. In the exemplary embodiment, therefore, the catalyst temperature is estimated based on a record of changes in the operation state of the internal combustion engine 10. Needless to say, it is possible to provide a temperature sensor in or in the vicinity of the catalyst 18 and calculate the reference value based on the catalyst temperature detected by the temperature sensor.

As described above, in the exemplary embodiment, monitoring of the output of the oxygen sensor for the abnormality diagnosis is inhibited for a predetermined time period after the stop of the fuel-cut operation in accordance with the condition (c5). The monitoring inhibition period is set so as to be changed depending on the total value of the intake air quantity during the fuel-cut operation and the estimated value of the catalyst temperature. The abnormality diagnosis may be resumed immediately after a point of time when release of oxygen from the catalyst 18 after stop of the fuel-cut operation becomes less influential to the abnormality diagnosis.

Further, in the exemplary embodiment, monitoring of the sensor output for the abnormality diagnosis is inhibited unless the temperature of the detector is equal to or higher than the activation temperature thereof in accordance with the condition (c6). This may effectively prevent the diagnosis error owing to the output voltage of the rear oxygen sensor 20 in the state where the temperature of the detector is not sufficiently increased.

A temperature sensor may be provided in or in the vicinity of the rear oxygen sensor 20 such that the temperature of the detector of the rear oxygen sensor 20 is detected. The temperature of the detector may be estimated on the basis of a record of change in the operation state of the internal combustion engine 10 just in the same way as in the case for measuring the catalyst temperature.

In this exemplary embodiment, the abnormality diagnosis is implemented on the basis of the output pattern of the rear oxygen sensor 20 under the condition where the precondition is satisfied by excluding the output pattern that is not appropriate for the abnormality diagnosis, for example, the output pattern obtained at a time point immediately after the stop of the fuel-cut operation, or a time point when the temperature of the detector is low. The accuracy of the abnormality diagnosis may be improved by restricting the monitoring of the sensor output in both cases where the abnormality diagnosis is implemented on the basis of the output frequency of the oxygen sensor distributed in the respective voltage regions as in the first exemplary embodiment, and the abnormality diagnosis is implemented on the basis of the time period for which the lean signal is continuously generated.

Decrease in the sensor output when the detector temperature is low may deteriorate the accuracy of the abnormality diagnosis irrespective of the position at which the oxygen sensor is provided. As a result, the sensor output generated when the detector temperature is lower than the activation temperature is not reflected in the abnormality diagnosis by detecting the fracture of the detector in the front oxygen sensor 19.

(1) In this exemplary embodiment, the quantity of oxygen absorbed in the catalyst 18 during the fuel-cut operation is obtained. The time period for which monitoring is inhibited after the stop of the fuel-cut operation is set to a value on the basis of the obtained quantity of the absorbed oxygen. This makes it possible to set the monitor inhibiting time period after the stop of the fuel-cut operation to a minimum value. Accordingly, reduction in the opportunity for implementing the abnormality diagnosis may be restrained while effectively avoiding the diagnosis error.

(2) In this exemplary embodiment, the monitoring inhibiting time period is set to a value that changes depending on the total value of the intake air quantity during the fuel-cut operation and the estimated value of the catalyst temperature. This makes it possible to obtain the quantity of the oxygen absorbed in the catalyst 18 during the fuel-cut operation, based on which the monitoring inhibiting time period is appropriately set.

In this exemplary embodiment, a temperature of the detector is detected. The abnormality diagnosis system is structured not to reflect the output of the rear oxygen sensor 20 obtained when the detected temperature of the detector is lower than the activating temperature in the diagnosis. This may avoid the abnormality diagnosis error on the basis of insufficient output of the rear oxygen sensor 20 owing to the low temperature of the detector.

Third Exemplary Embodiment

Next, a third exemplary embodiment will be described referring to FIG. 10, focusing on the feature different from those of the first and the second exemplary embodiments.

As described above, when the detector of the oxygen sensor 19 or 20 is fractured, the difference in the oxygen partial pressure between the inside and outside of the detector becomes substantially zero. Therefore the oxygen sensor 19 or 20 hardly generates the output voltage. However, when the oxygen partial pressure of the exhaust gas decreases abruptly, the exhaust gas at a low oxygen partial pressure exists in the outside of the detector while the exhaust gas at a high oxygen partial pressure exists in the inside of the detector until the exhaust gas on the outside of the detector enters into the inside of the detector. As a result, the oxygen sensor 19 or 20 temporarily generates the high output voltage even when the detector of the oxygen sensor 19 or 20 is fractured.

When the oxygen partial pressure of the exhaust gas increases abruptly in the case where the detector of the oxygen sensor is fractured, the exhaust gas at low oxygen partial pressure remains inside of the detector, and the oxygen partial pressure of the exhaust gas existing on the outside of the detector becomes high. As a result, the difference of the oxygen partial pressure occurs between the inside and outside of the detector. In this case, the oxygen in an ionized state moved from the outside to the inside of the detector as shown in FIG. 1. As a result, electricity flows in a direction opposite to the normal direction such that negative voltage is generated by the oxygen sensor 19 or 20 as shown by an arrow of FIG. 5C.

However, it is unlikely that the oxygen partial pressure of the combusted exhaust gas becomes higher than that of the atmosphere inside of the detector. Accordingly, it is impossible for the oxygen sensor 19, 20 having no fractured detector to generate negative output voltage. Therefore, it is determined that the detector is fractured when the output of the oxygen sensor 19 or 20 indicates that the oxygen partial pressure of the outside of the detector (exhaust gas) is higher than that of the inside of the detector (atmosphere).

Figure 10:
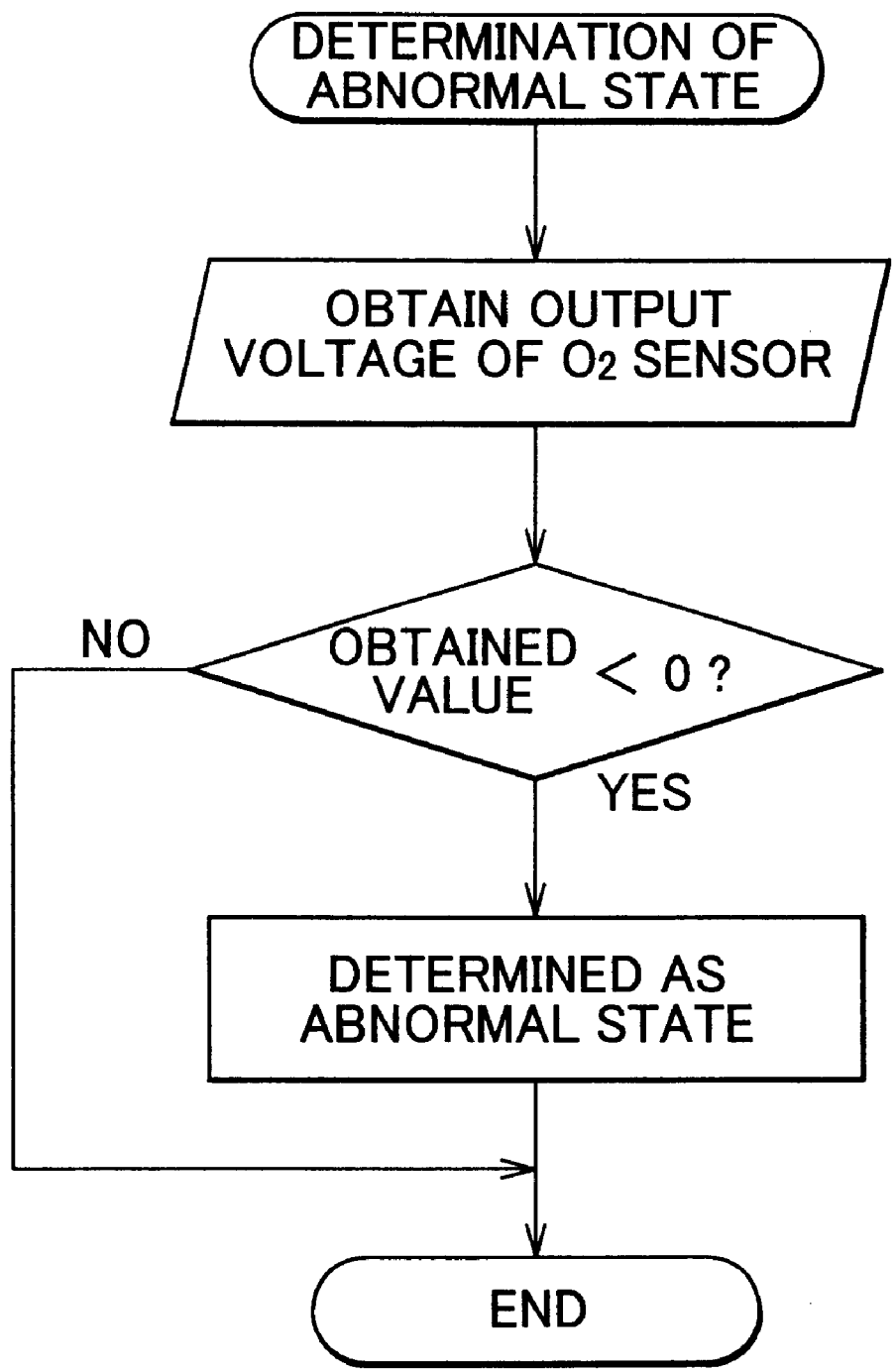
FIG. 10 is a flowchart showing a control routine for the abnormality diagnosis in another exemplary embodiment of the invention.

In this exemplary embodiment, the abnormality diagnosis is implemented as shown in a flowchart of FIG. 10, where it is determined that the detector of the oxygen is fractured when the negative voltage is generated by the oxygen sensor 19 or 20, that is, the output voltage generated by the oxygen sensor 19 or 20 that has been sampled is equal to or lower than "0". As a result, the diagnosis of this exemplary embodiment allows easy and quick detection of the fracture in the detector of the oxygen sensor 19 or 20.

In the aforementioned exemplary embodiment, the output voltage generated by the rear oxygen sensor 20 is distributed in four output voltage regions. Each output frequency distributed in the respective voltage regions is counted by the corresponding counters Ca to Cd so as to obtain the output frequency of the rear oxygen sensor 20 distributed in the respective voltage regions. However, the method for obtaining the output frequency distributed in the respective regions is not limited.

Further, the normality/abnormality determination condition in the exemplary embodiment may be modified in accordance with output characteristics of the oxygen sensor to be monitored. Characteristics of the output patterns of the oxygen sensor at its normal state and abnormal state are distinguished such that the normality/abnormality determination is performed. This makes it possible to accurately detect the abnormality on the basis of the aforementioned output pattern even when the oxygen sensor with the fractured detector temporarily generates the detection signal similar to that generated by the oxygen sensor in the normal state, or the oxygen sensor in the normal state temporarily generates the detection signal similar to that generated by the oxygen sensor in the abnormal state.

In another exemplary embodiment, the reference value of the time elapsing after the stop of the fuel-cut operation is calculated on the basis of the total value of the intake air quantity during the fuel-cut operation and the catalyst temperature. Based on the calculated reference value, the monitoring inhibiting time period for which monitoring of the sensor output after the stop of the fuel-cut operation is inhibited is set. However, the quantity of oxygen absorbed in the catalyst 18 during the fuel-cut operation can be estimated on the basis of either one of the total value of the intake air quantity during the fuel-cut operation or the catalyst temperature. Accordingly, the monitoring inhibiting time period may be set in accordance with the estimated quantity of oxygen absorbed in the catalyst 18. Other parameters may be used to estimate the quantity of oxygen absorbed in the catalyst 18, based on which the monitoring inhibiting time period is set.

In this exemplary embodiment, the abnormality diagnosis is suspended when the precondition become unsatisfied, and the diagnosis is resumed from the beginning when the precondition becomes satisfied again. Alternatively, while the precondition is being unsatisfied, monitoring of the sensor output of the oxygen sensor in the diagnosis may only be suspended. That is, while the precondition is being unsatisfied, the diagnosis is suspended, and then is resumed when the precondition becomes satisfied. The accuracy of the diagnosis may be improved by inhibiting the sensor output from being reflected after the stop of the fuel-cut operation when the detector temperature is low or until an elapse of time set in accordance with the quantity of oxygen absorbed in the catalyst 18 during the fuel-cut operation.

In the exemplary embodiment, the output of the oxygen sensor is inhibited from being reflected in the abnormality diagnosis after the stop of the fuel-cut operation in both cases when the detector temperature is low or until an elapse of time set in accordance with the quantity of oxygen absorbed in the catalyst 18 during the fuel-cut operation. The accuracy of the abnormality diagnosis using the rear oxygen sensor disposed downstream of the catalyst 18 may be improved by inhibiting the sensor output from being reflected in the abnormality diagnosis after the stop of the fuel-cut operation only in the case until the time set in accordance with the quantity of oxygen absorbed in the catalyst elapses. Reduction in the accuracy of the abnormality diagnosis may be restrained by inhibiting the sensor output from being reflected in the abnormality diagnosis after stop of the fuel-cut operation only in the case when the detector temperature is lower than the activation temperature. The accuracy of the abnormality diagnosis may be further improved by inhibiting the output of the sensor disposed upstream of the catalyst from being reflected in the abnormality diagnosis in the case when the detector temperature is lower than the activation temperature.

In the abnormality diagnosis, not only the oxygen sensor as shown in FIG. 1 is employed but also any type of sensor may be employed so long as the sensor has a detector interposed between the exhaust gas and the reference gas, and is capable of generating the detection signal in accordance with the difference of the oxygen partial pressure between the exhaust gas and the reference gas.

The abnormality diagnosis of the aforementioned exemplary embodiments may be applied not only to the oxygen sensor employed in the exhaust gas purification system as shown in FIG. 3 but also to the oxygen sensor employed in any type of the exhaust gas purification system.

The ECU 22 of the illustrated exemplary embodiments is implemented as one or more programmed general purpose computers. It will be appreciated by those skilled in the art that the controller can be implemented using a single special purpose integrated circuit (e.g., ASIC) having a main or central processor section for overall, system-level control, and separate sections dedicated to performing various different specific computations, functions and other processes under control of the central processor section. The controller can be a plurality of separate dedicated or programmable integrated or other electronic circuits or devices (e.g., hardwired electronic or logic circuits such as discrete element circuits, or programmable logic devices such as PLDs, PLAs, PALs or the like). The controller can be implemented using a suitably programmed general purpose computer, e.g., a microprocessor, microcontroller or other processor device (CPU or MPU), either alone or in conjunction with one or more peripheral (e.g., integrated circuit) data and signal processing devices. In general, any device or assembly of devices on which a finite state machine capable of implementing the procedures described herein can be used as the controller. A distributed processing architecture can be used for maximum data/signal processing capability and speed.

While the invention has been described with reference to preferred exemplary embodiments thereof, it is to be understood that the invention is not limited to the disclosed embodiments or constructions. On the contrary, the invention is intended to cover various modifications and equivalent arrangements. In addition, while the various elements of the disclosed invention are shown in various combinations and configurations, which are exemplary, other combinations and configurations, including more less or only a single element, are also within the spirit and scope of the invention.

What is claimed is:

1. A diagnosis system that determines an abnormality in at least one oxygen sensor, having a detector interposed between a reference gas and an exhaust gas and generating a detection signal in accordance with a difference of an oxygen partial pressure between the reference gas and the exhaust gas, the system comprising:

a controller that determines the abnormality of the oxygen sensor owing to a fracture of the detector on the basis of an output pattern of the detection signal of the oxygen sensor, wherein the controller determines whether the detector has the fracture on the basis of a distribution pattern of the detection signal generated by the oxygen sensor.

2. A diagnosis system according to claim 1, wherein the oxygen sensor is provided in an exhaust passage of an internal combustion engine, and the controller performs a feedback control of an air-fuel injection quantity such that an air-fuel ratio of an air-fuel mixture supplied to the internal combustion engine is maintained in the vicinity of a stoichiometric air-fuel ratio on the basis of the detection signal of the oxygen sensor.

3. A diagnosis system according to claim 1, wherein the oxygen sensor is a solid electrolyte oxygen sensor.

4. A diagnosis system according to claim 1, wherein the controller determines that the detector is fractured when it is determined that a ratio of a detection signal indicating the difference of the oxygen partial pressure that is equal to or less than a first predetermined value to the detection signal of the oxygen sensor becomes equal to or greater than a second predetermined value.

5. A diagnosis system according to claim 1, wherein the controller determines that the detector is not fractured when it is determined that a ratio of a detection signal indicating the difference of the oxygen partial pressure that is equal to or greater than a third predetermined value to the detection signal of the oxygen sensor becomes equal to or greater than a fourth predetermined value.

6. A diagnosis system according to claim 1, wherein:
wherein the controller detects a temperature of the detector and inhibits the detection signal of the oxygen sensor from being used for determining the abnormality of the oxygen sensor when the detected temperature is lower than an activating temperature of the detector.

7. A diagnosis system according to claim 6, wherein the oxygen sensor is a solid electrolyte oxygen sensor.

8. A diagnosis system that determines an abnormality in at least one oxygen sensor provided downstream of a catalyst of an exhaust system in an internal combustion engine, the oxygen sensor having a detector interposed between an atmosphere and an exhaust gas, and generating a detection signal in accordance with a difference of an oxygen partial pressure between the atmosphere and the exhaust gas, the system comprising:
a controller that determines the abnormality of the oxygen sensor owing to a fracture of the detector on the basis of an output pattern of the detection signal of the oxygen sensor, wherein the controller inhibits the detection signal of the oxygen sensor from being used for determining the abnormality of the oxygen sensor until a predetermined period of time elapses from a point of time when a fuel-cut operation of the internal combustion engine is stopped, calculates a quantity of oxygen absorbed by the catalyst during the fuel-cut operation and sets the predetermined period of time to a value that changes depending upon the calculated quantity of oxygen absorbed by the catalyst.

9. A diagnosis system according to claim 8, wherein the oxygen sensor is a solid electrolyte oxygen sensor.

10. A diagnosis system that determines an abnormality in at least one oxygen sensor provided downstream of a catalyst of an exhaust system in an internal combustion engine, the oxygen sensor having a detector that isolates an atmosphere from an exhaust gas, and generating a detection signal in accordance with a difference of an oxygen partial pressure between the atmosphere and the exhaust gas, the system comprising:
a controller that determines the abnormality of the oxygen sensor owing to a fracture of the detector on the basis of an output pattern of the detection signal of the oxygen sensor, wherein the controller inhibits the detection signal of the oxygen sensor from being used for determining the abnormality of the oxygen sensor until a predetermined period of time elapses from a point of time when a fuel-cut operation of the internal combustion engine is stopped and sets the predetermined period of time in accordance with at least one of a total value of an intake air quantity into the engine during the fuel-cut operation and a catalyst temperature.

11. A diagnosis system according to claim 10, wherein the oxygen sensor is a solid electrolyte oxygen sensor.

12. A diagnosis system that determines an abnormality in at least one oxygen sensor having a detector interposed between an atmosphere and an exhaust gas and generating a detection signal in accordance with a difference of an oxygen partial pressure between the atmosphere and the exhaust gas, the system comprising:
a controller that determines the abnormality of the oxygen sensor owing to a fracture of the detector on the basis of an output pattern of the detection signal of the oxygen sensor, wherein the controller determines that the detector is fractured upon generation of the detection signal of the oxygen sensor, which indicates that the oxygen partial pressure of the exhaust gas is higher than that of the atmosphere.

13. A method for determining an abnormality in at least one oxygen sensor having a detector interposed between a reference gas and an exhaust gas, comprising:
generating a detection signal in accordance with a difference of an oxygen partial pressure between the reference gas and the exhaust gas; and
determining the abnormality of the oxygen sensor owing to a fracture of the detector on the basis of an output pattern of the generated detection signal, wherein the detector is determined to have the fracture on the basis of a distribution pattern of the generated detection signal.

14. A method according to claim 13, wherein the oxygen sensor is provided in an exhaust passage of an internal combustion engine, and an air-fuel injection quantity is feedback controlled such that an air-fuel ratio of an air-fuel mixture supplied to the internal combustion engine is maintained in the vicinity of a stoichiometric air-fuel ratio on the basis of the detection signal of the oxygen sensor.

15. A method according to claim 13, wherein the detector is determined to have the fracture when it is determined that a ratio of a detection signal indicating the difference of the oxygen partial pressure that is equal to or less than a first predetermined value to the generated detection signal becomes equal to or greater than a second predetermined value.

16. A method according to claim 13, wherein the detector is determined not to have the fracture when it is determined that a ratio of a detection signal indicating the difference of the oxygen partial pressure that is equal to or greater than a third predetermined value to the generated detection signal becomes equal to or greater than a fourth predetermined value.

17. A method according to claim 13, wherein a temperature of the detector is detected and the generated detection signal is inhibited from being used for determining the abnormality of the oxygen sensor when the detected temperature is lower than an activating temperature of the detector.

18. A method for determining an abnormality in at least one oxygen sensor provided downstream of a catalyst of an exhaust system in an internal combustion engine, the oxygen sensor having a detector interposed between an atmosphere and an exhaust gas, comprising:
generating a detection signal in accordance with a difference of an oxygen partial pressure between the atmosphere and the exhaust gas; and
determining the abnormality of the oxygen sensor owing to a fracture of the detector on the basis of an output pattern of the generated detection signal, wherein the generated detection signal is inhibited from being used for determining the abnormality of the oxygen sensor until a predetermined period of time elapses from a point of time when a fuel-cut operation of the internal combustion engine is stopped, a quantity of oxygen absorbed by the catalyst during the fuel-cut operation is calculated and the predetermined period of time is set to a value that changes depending upon the calculated quantity of oxygen absorbed by the catalyst.

19. A method for determining an abnormality in at least one oxygen sensor provided downstream of a catalyst of an exhaust system in an internal combustion engine, the oxygen sensor having a detector that isolates an atmosphere from an exhaust gas, comprising:

generating a detection signal in accordance with a difference of an oxygen partial pressure between the atmosphere and the exhaust gas; and determining the abnormality of the oxygen sensor owing to a fracture of the detector on the basis of an output pattern of the generated detection signal, wherein the generated detection signal is inhibited from being used for determining the abnormality of the oxygen sensor until a predetermined period of time elapses from a point of time when a fuel-cut operation of the internal combustion engine is stopped and the predetermined period of time is set in accordance with at least one of a total value of an intake air quantity into the engine during the fuel-cut operation and a catalyst temperature.

20. A method for determining an abnormality in at least one oxygen sensor having a detector interposed between an atmosphere and an exhaust gas, comprising:

generating a detection signal in accordance with a difference of an oxygen partial pressure between the atmosphere and the exhaust gas; and determining the abnormality of the oxygen sensor owing to a fracture of the detector on the basis of an output pattern of the generated detection signal, wherein the detector is determined to be fractured upon generation of the detection signal which indicates that the oxygen partial pressure of the exhaust gas is higher than that of the atmosphere.

* * * * *

UNITED STATES PATENT AND TRADEMARK OFFICE
CERTIFICATE OF CORRECTION

PATENT NO. : 6,711,932 B2
DATED : March 30, 2004
INVENTOR(S) : Yasushi Iwazaki et al.

It is certified that error appears in the above-identified patent and that said Letters Patent is hereby corrected as shown below:

Title page,
Item [56], References Cited, U.S. PATENT DOCUMENTS,

-- 5,423,203   A    06/1995    Namiki et al. ..............073/001
   5,648,601   A    07/1997    Katoh et al. ................073/001
   5,781,878   A    07/1998    Mizoguchi et al. ...........701/109
   5,801,295   A    09/1998    Davey et al. ...............073/1.06
   5,819,195   A    10/1998    Iwata .......................701/103
   5,901,691   A    05/1999    Katoh .......................123/688
   5,970,967   A    10/1999    Uchikawa .................. 123/688
   5,927,260   A    07/1999    Kishimoto et al. ...........123/688
   6,176,080   B1   01/2001    Izumiura et al. ............060/276
   6,227,033   B1   05/2001    Kainz. .....................073/23.32
   6,258,232   B1   07/2001    Hasegawa et al. ...........204/424
   6,286,493   B1   09/2001    Aoki .......................123/690
   6,304,813   B1   10/2001    Ikeda et al. ................701/109
   6,343,499   B1   02/2002    Inagaki et al. .............073/23.32
   6,435,171   B2   08/2002    Kitajima et al. ............123/688 --

FOREIGN PATENT DOCUMENTS,

-- JP    A 5-125978    05/1993
   JP    A 5-256175    10/1993
   JP    A 8-21282     01/1996
   JP    A 10-10080    01/1998 --

Signed and Sealed this

Tenth Day of August, 2004

JON W. DUDAS
*Acting Director of the United States Patent and Trademark Office*